US012622655B2

(12) United States Patent
Ahnen et al.

(10) Patent No.: US 12,622,655 B2
(45) Date of Patent: May 12, 2026

(54) POSITRON EMISSION TOMOGRAPHY (PET)-SCANNING DEVICE

(71) Applicant: Positrigo AG, Zürich (CH)

(72) Inventors: Max Ludwig Ahnen, Zürich (CH); Jannis Nikolaus Rudolf Fischer, Zürich (CH); Ekaterina Mikhaylova, Riniken (CH)

(73) Assignee: Positrigo AG, Zurich (CH)

( * ) Notice: Subject to any disclaimer, the term of this patent is extended or adjusted under 35 U.S.C. 154(b) by 263 days.

(21) Appl. No.: 18/031,402

(22) PCT Filed: Oct. 11, 2021

(86) PCT No.: PCT/EP2021/077986
§ 371 (c)(1),
(2) Date: Apr. 12, 2023

(87) PCT Pub. No.: WO2022/078928
PCT Pub. Date: Apr. 21, 2022

(65) Prior Publication Data
US 2023/0371906 A1 Nov. 23, 2023

(30) Foreign Application Priority Data
Oct. 13, 2020 (EP) ..................................... 20201569

(51) Int. Cl.
*A61B 6/03* (2006.01)
*A61B 6/42* (2024.01)
*G01T 1/29* (2006.01)

(52) U.S. Cl.
CPC ............ *A61B 6/037* (2013.01); *A61B 6/4258* (2013.01); *G01T 1/2985* (2013.01); *G06T 2207/10104* (2013.01)

(58) Field of Classification Search
CPC ...................................................... A61B 6/037
See application file for complete search history.

(56) References Cited

U.S. PATENT DOCUMENTS 5,617,856 A 4/1997 Tamura et al.
7,884,331 B2 2/2011 Majewski et al.
(Continued)

FOREIGN PATENT DOCUMENTS

CN 109864751 A 6/2019
EP 2 903 524 A1 8/2015
(Continued)

OTHER PUBLICATIONS

Yamamoto et al. Development of a Brain PET System, PET-Hat: A Wearable PET System for Brain Research , IEEE Transactions on Nuclear Science, vol. 58, No. 3, pp. 668-673 (Year: 2011).*
(Continued)

*Primary Examiner* — Uzma Alam
*Assistant Examiner* — Shun Lee
(74) *Attorney, Agent, or Firm* — Sughrue Mion, PLLC

(57) ABSTRACT

A positron emission tomography (PET)-scanning device is provided, having a detector ring for detecting emitted PET-radiation and a main supporting structure which has or to which is attached a U-shaped portion with two arms for holding the detector ring between the arms. The detector
(Continued)

Figure 1:
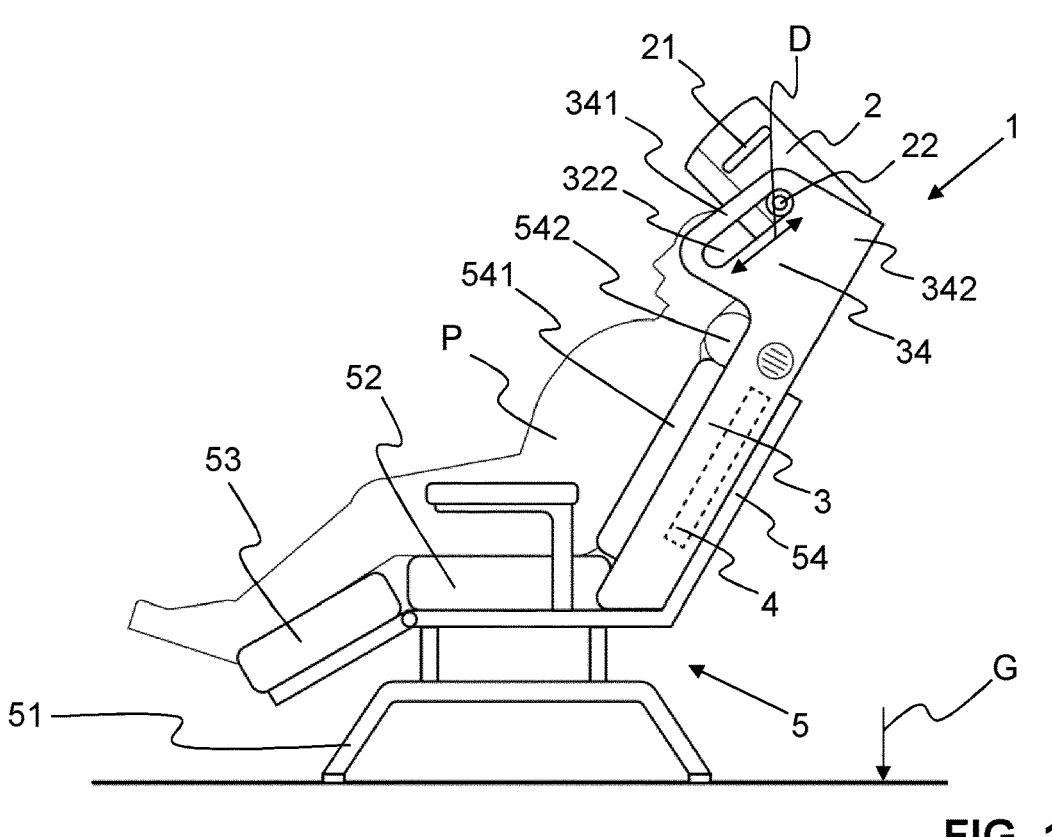

ring is held by the two arms in such a way that the detector ring can be rotated about an axis of rotation that extends through the U-shaped portion, in particular through the two arms of the U-shaped portion.

18 Claims, 8 Drawing Sheets

(56)                    References Cited

U.S. PATENT DOCUMENTS

| 8,735,834 | B2 | 5/2014 | Millett et al. |
| 9,226,717 | B2 | 1/2016 | Tashima et al. |
| 9,414,789 | B2 | 8/2016 | Soluri et al. |
| 9,833,208 | B2 | 12/2017 | Amano |
| 10,307,120 | B1 | 6/2019 | Thomas et al. |
| 10,531,843 | B2 | 1/2020 | Gatayama et al. |
| 10,653,374 | B1* | 5/2020 | Thomas ............... A61B 6/4447 |
| 12,171,540 | B2 | 12/2024 | Jang |
| 2010/0020919 | A1* | 1/2010 | Dragan ................ A61B 6/4441 |
| | | | 250/336.1 |
| 2011/0315884 | A1 | 12/2011 | Worstell et al. |
| 2012/0324646 | A1* | 12/2012 | Briganti ............... A47G 9/0246 |
| | | | 5/496 |
| 2012/0324648 | A1* | 12/2012 | Amano ................ A61B 6/4482 |
| | | | 5/601 |
| 2013/0218010 | A1 | 8/2013 | Weinberg et al. |
| 2016/0166219 | A1 | 6/2016 | Majewski et al. |
| 2018/0011153 | A1 | 1/2018 | Pourrahimi |
| 2018/0199853 | A1 | 7/2018 | Abkai et al. |
| 2024/0324976 | A1 | 10/2024 | Fischer et al. |
| 2024/0389959 | A1* | 11/2024 | Fischer .................. A61B 6/105 |
| 2025/0009315 | A1 | 1/2025 | Ahnen et al. |

FOREIGN PATENT DOCUMENTS

| JP | 2000-214263 | A | 8/2000 |
| JP | 3244776 | B2 | 1/2002 |
| JP | 3793320 | B2 | 7/2006 |
| JP | 2010-223956 | A | 10/2010 |
| JP | 4642143 | B2 | 3/2011 |
| WO | 2014/058772 | A1 | 4/2014 |
| WO | 2018/098147 | A1 | 5/2018 |
| WO | 2020/015384 | A1 | 1/2020 |

OTHER PUBLICATIONS

Seiichi Yamamoto, et al., "Development of a Brain PET System, PET-Hat: A Wearable PET System for Brain Research", IEEE Transactions on Nuclear Science, XP011477455, Jun. 2011, pp. 668-673, vol. 58, No. 3.
International Search Report for PCT/EP2021/077986 dated Nov. 11, 2021 (PCT/ISA/210).
Written Opinion for PCT/EP2021/077986 dated Nov. 11, 2021 (PCT/ISA/237).
"A Look Behind the Machines—How does on make a PET scanner?" Motion Artifacts, Blog by Pearl Technology, Dec. 15, 2023, (9 pages).
FDA, FDA 501K Response from the US Food and Drug Administration dated Jul. 15, 2024, Retrieved from Internet: https://ww.accessdata.fda.gov/cdrh_docs/pdf24/K241751.pdf, (15 pages).

* cited by examiner

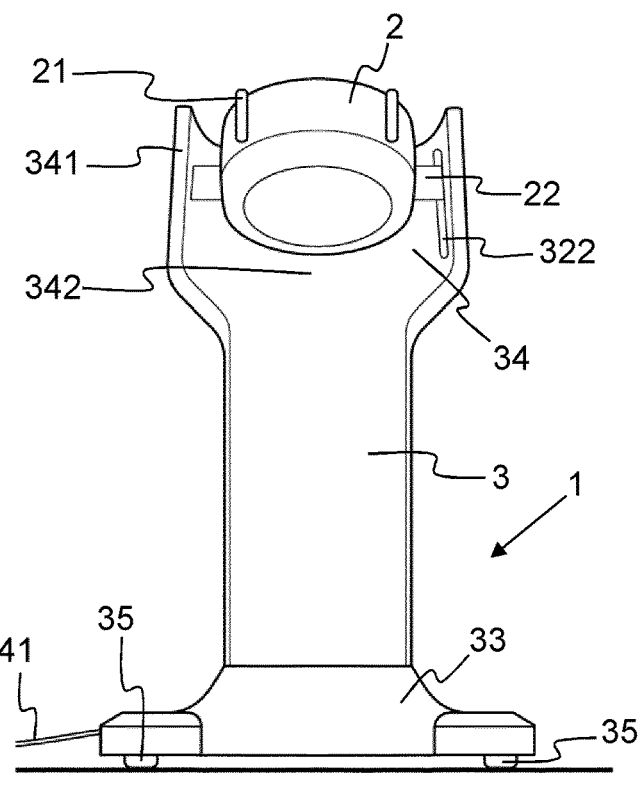
FIG. 2b
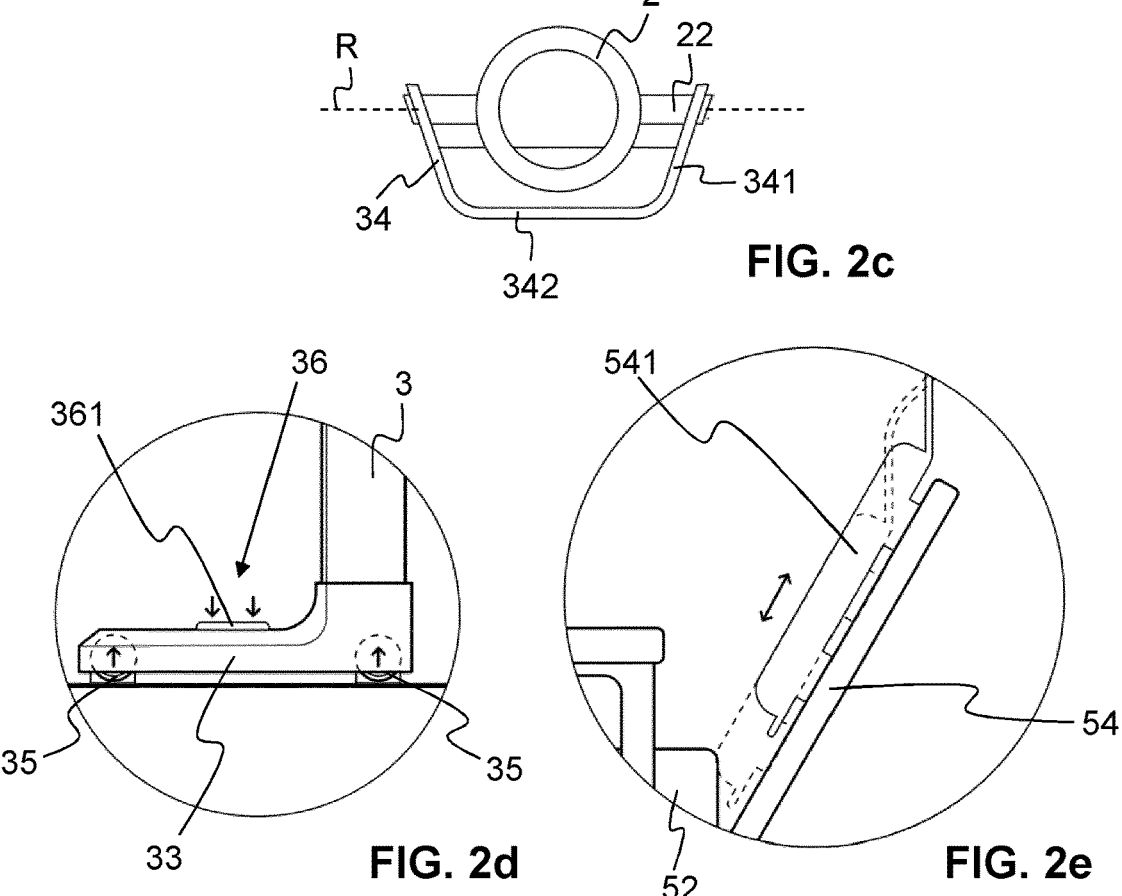
FIG. 2c
FIG. 2d
FIG. 2e

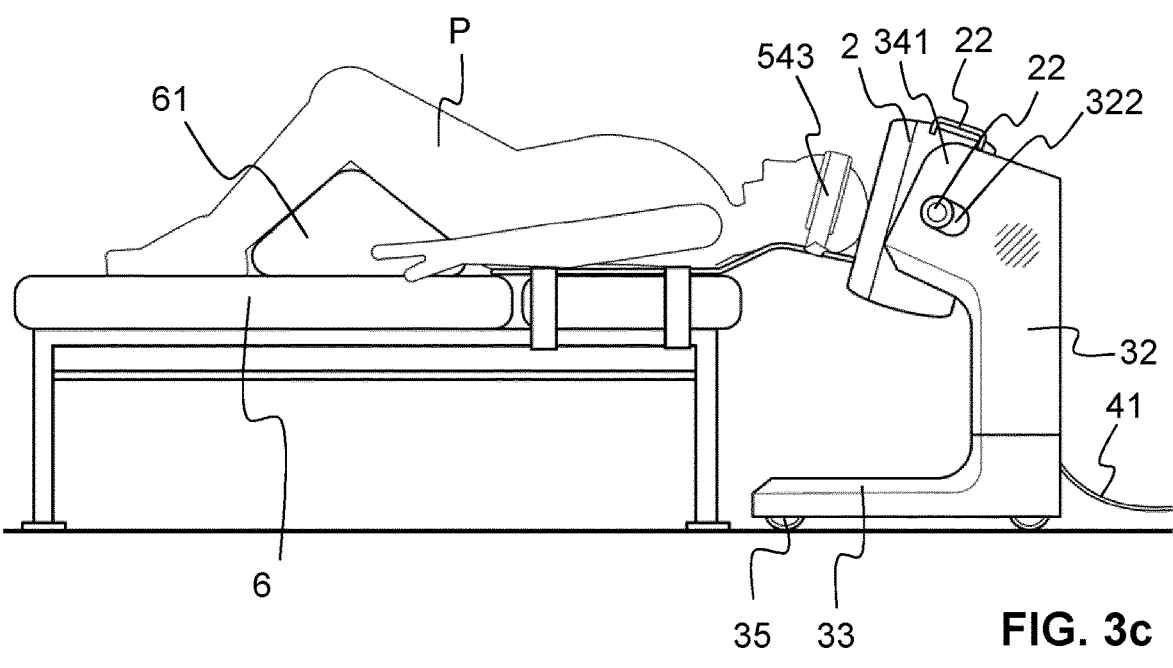
FIG. 3c
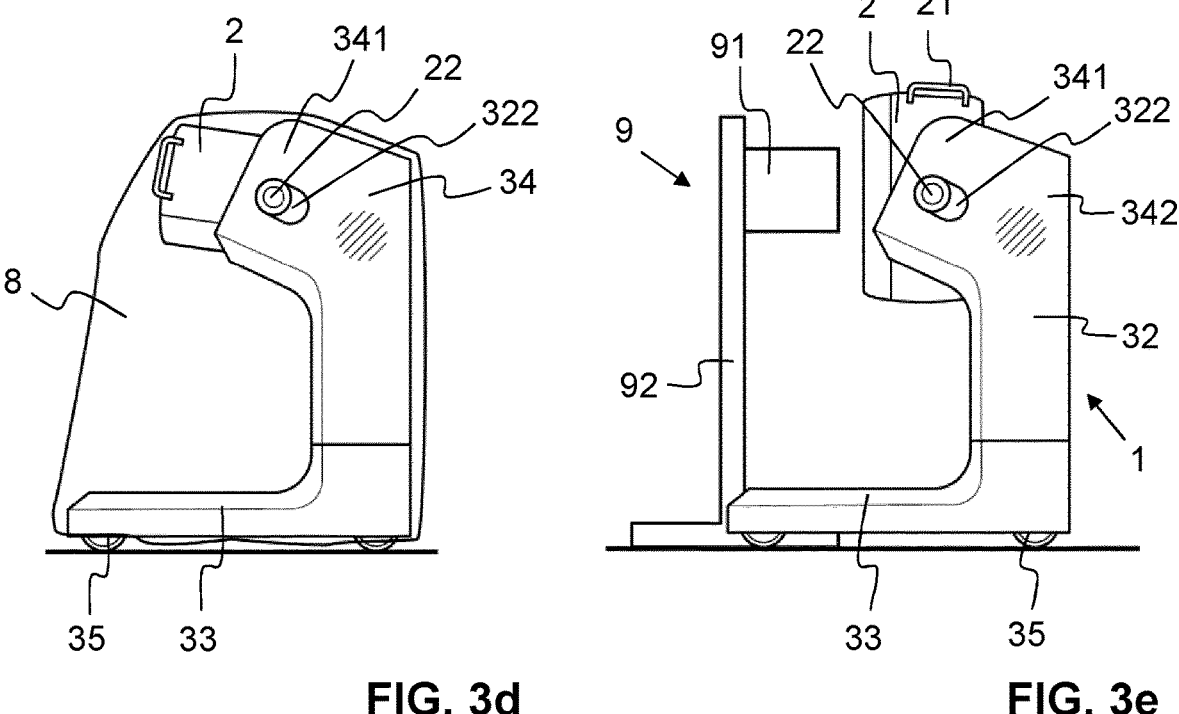
FIG. 3d
FIG. 3e

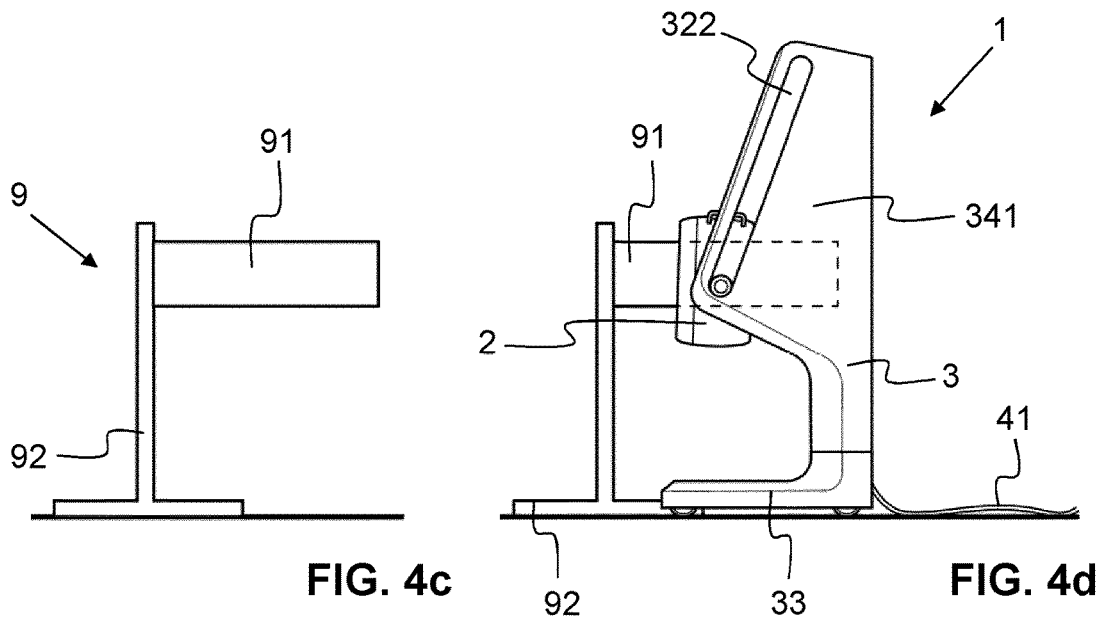
FIG. 4c
FIG. 4d
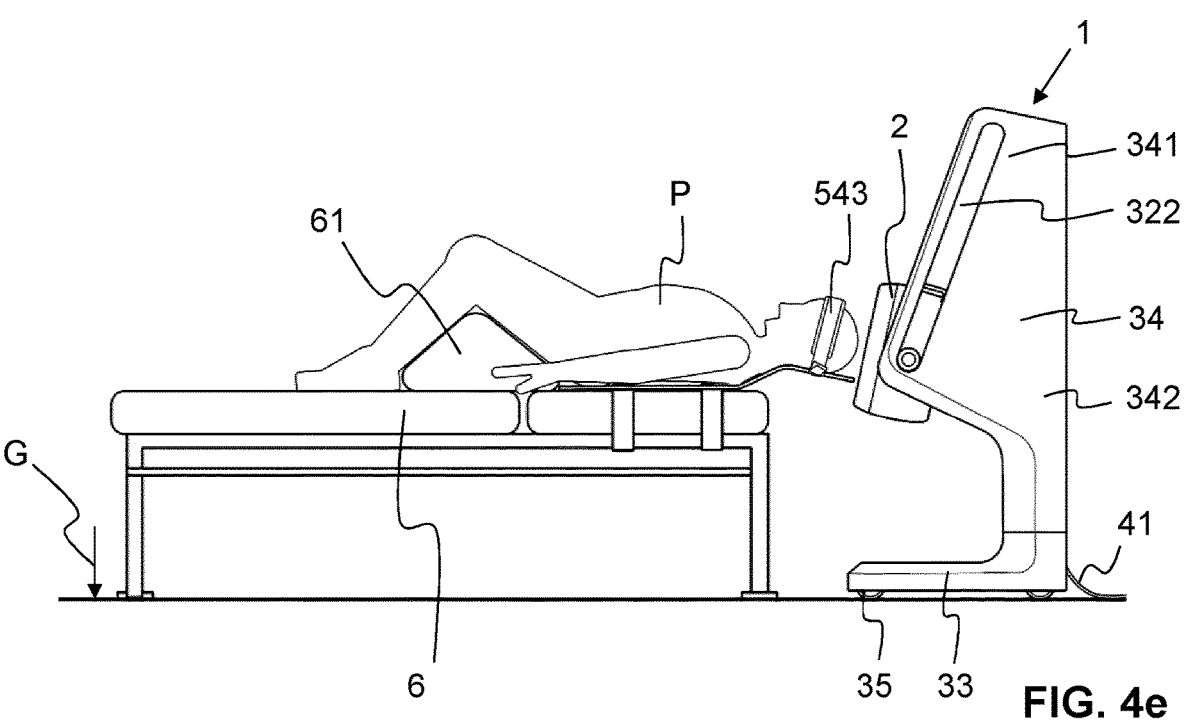
FIG. 4e

POSITRON EMISSION TOMOGRAPHY (PET)-SCANNING DEVICE

CROSS REFERENCE TO RELATED APPLICATIONS

This application is a National Stage of International Application No. PCT/EP2021/077986 filed Oct. 11, 2021, claiming priority based on European Patent Application No. 20201569.9 filed Oct. 13, 2020.

TECHNICAL FIELD

The present invention concerns a positron emission tomography (PET)-scanning device, which is particularly well adaptable to the needs of the subject to be scanned. The PET-scanning device can particularly be a movable device on wheels.

PRIOR ART

Positron emission tomography (PET)-scanning devices are usually big and bulky and only available at hospitals or at dedicated radiology facilities. As a consequence, patients have to travel to the place of the PET-scanning device, in order to be scanned, if required. The patients, however, are often elderly or sick people who live in a nursing home, cannot move well or are confined to bed. As a result, the travel to the PET-scanning location is cumbersome for the patients and often involves a not inconsiderable risk that the patient may have a complication while traveling or becomes infected, for example. The PET-scanning device also requires the patient to assume a certain position, usually a position lying on the back, on a bed during the scanning procedure. Depending on his state of health, this position can be quite a burden for the patient, which can even impair the scanning result, if the patient e.g. moves during the scanning.

Furthermore, hospitals, researchers, material scientists and veterinarians have no good access to PET-machines, not only because they are too big, but also because they often do not fit their needs in particular with regard to applications outside of the standard oncology applications in the hospital clinic.

Thus, most state of the art PET-scanning machines have the drawback that they cannot be brought to subjects and are not versatile for different purposes.

US 2013/0218010 A1 discloses a compact and light-weight PET-scanner which is portable and can be affixed to a patient bed.

In WO 2020/015384 A1, U.S. Pat. No. 9,226,717 B2, U.S. Pat. No. 7,884,331 B2 and CN 109864751 A, a PET-detector is disclosed that is integrated in a helmet-like brain imager. The PET brain imager is suspended from a mobile gantry.

U.S. Pat. No. 9,833,208 B2 discloses a PET-imaging device with an adjustable support table, which allows the patient to either sit, lie or stand during the imaging procedure.

The PET-scanning device as disclosed in U.S. Pat. No. 10,307,120 B1 comprises a horizontally positioned and vertically movable detector ring which enables the patient to sit upright in a wheel chair during the scanning process.

JP 3244776 B2 shows a computer tomography (CT)-machine with a gantry body that can be inclined by rotating it about an upper, horizontally extending axis, in order to enable a scanning of patients in both sitting and lying positions.

U.S. Pat. No. 10,531,843 B2 proposes to combine a CT apparatus having a horizontally rotatable gantry device with an adjustable scanning support that allows the patient to adopt any of a variety of different positions during the imaging process.

U.S. Pat. No. 9,414,789 B2 shows a PET-imaging device with reduced dimensions. The device comprises a plurality of measuring rings with different diameters, which are slidably mounted on a support structure.

US 2011/0315884 A1 discloses a mobile PET-scanner on wheels for imaging the human head. Another mobile PET-scanner on wheels is disclosed by U.S. Pat. No. 8,735,834 B2.

JP 4642143 B2 discloses a PET-scanning device with a detector ring that is held between two arms which are suspended via a pulley on a ceiling or via linked rods on a wall or on a wheel chair.

US 2016/0166219 A1 is directed to a device that combines a virtual reality system with PET-brain imaging. A mobile brain imager is suspended on a mobile support which can be carried in the form of a backpack or which can be arranged on a carriage having wheels.

JP 3793320 B2 shows a CT-machine having a U-shaped support structure to which two vertically movable holding arms are attached. A rotatable imaging unit is held between the two arms.

WO 2014/058772 A1 discloses an apparatus for cone beam computed tomography having a gimballed scanner device that houses source and detector. The scanner device is movable along a vertical support column.

SUMMARY OF THE INVENTION

It is an object of the present invention to provide a versatile positron emission tomography (PET)-scanning device which can be easily adapted to the needs of the subject to be scanned.

For the purposes of this document, height and directional information, such as "top", "bottom", "up", "down", "upwards", "downwards", etc., shall be understood to refer to a PET-scanning device which, in its normal and intended use, stands upright in relation to the direction of gravity, ready to scan a human or animal subject or a plant.

In order to achieve this object, the present invention provides a positron emission tomography (PET)-scanning device comprising a detector ring for detecting emitted PET-radiation;

a main supporting structure which has or to which is attached a U-shaped portion with two arms for holding the detector ring between the arms;

wherein the detector ring is held by the two arms in such a way that the detector ring can be rotated about an axis of rotation that extends through the U-shaped portion, in particular through the two arms of the U-shaped portion. Furthermore, the detector ring is preferably held by the two arms in such a way that the detector ring can be displaced, in particular translationally displaced, relative to the main supporting structure, preferably relative to two arms.

The extension of the axis of rotation of the detector ring through the two arm brings about the advantage that the detector ring can be adjusted easily to the patient's needs by means of rotation, while at the same time be held in a particularly stable way on the main supporting structure. A further adjustment to the patient is preferably possible by displacing the detector ring relative to the two arms. If the detector ring is displaceable relative to the two arms, instead of e.g. with the two arms, no unnecessary elements need to be displaced with the detector ring, which allows to reduce the total weight of the displaceable parts and to make the displacement of the detector ring easier for the user. Of course, it is conceivable that in certain embodiments, the detector ring is displaceable not only relative to the two arms, but also with the two arms.

The detector ring usually comprises a plurality of sensors, in particular a plurality of sensor modules, which are arranged in a circumferential ring, in order to be positioned around e.g. a patient's head for detecting PET-radiation emitted from the patient's brain.

The detector ring usually has a round, for example oval or circular, shape at least at its inner surface. Thus, the detector ring usually and preferably has a round, in particular circular, opening, into which the part to be scanned of the subject is inserted for the PET-scanning. The outer surface of the detector ring preferably also forms a round, in particular circular, shape. A detector ring having such a form has a more lightweight look in the eyes of the user. The detector ring can, however, also have an angular, in particular rectangular or squared, inner or outer shape.

The detector ring advantageously has at least one handle for facilitating rotation and displacement of the detector ring for the user.

The PET-scanning device does not necessarily have to be adapted to scan human patients, in particular human brains, only. It can also be suited to scan extremities, such as arms and legs, and/or to scan animals or plants. The possibility to rotate and displace the detector ring relative to the main supporting structure makes the PET-scanning device particularly versatile and adaptable to different purposes, such as to e.g. the scanning of rodents or of plants.

In normal use of the PET-scanning device, the main supporting structure usually carries the main weight, if not the entire weight, of the detector ring. Thus, the main supporting structure usually serves to support and to hold the detector ring in a stable position during the scanning procedure. After having positioned the main supporting structure close to the subject to be scanned or vice versa, the detector ring can be rotated and displaced accordingly, in order to fine-adjust the PET-scanning device to the subject.

The U-shaped portion is defined by the two arms in particular. The two arms are usually connected to each other at one end by means of a perpendicularly extending connection portion, which also forms a part of the U-shaped portion. The other end of each arm usually forms a free end. The axis of rotation extends through the U-shaped portion, if it extends through at least one out of the two arms and the connection portion. Preferably, the axis of rotation extends through each of the two arm or through the connection portion. Particularly preferred are embodiments in which the axis of rotation extends in a perpendicular direction with respect to the direction of extension of two arms, more preferred in parallel to the connection portion.

The two arms and the connection portion preferably define a plane within which the U-shaped portion is arranged. The plane can have a certain thickness. Elements that are not arranged within this plane and that particularly extend in a perpendicular direction relative to this plane are normally not considered to be part of the U-shaped portion, in particular, if these elements are displaceably attached. The U-shaped portion is preferably formed as a whole in a single piece.

The direction of displacement can extend in a direction that is inclined or even perpendicular to the plane spanned by the two arms and the connection portion of the U-shaped portion. In certain embodiments, the direction of displacement can also extend in parallel to the two arms. In order to be optimally adjustable to the desired imaging plane, the detector ring is advantageously, in at least one rotation position, displaceable in a direction that stands approximately perpendicular to the plane defined by opening of the detector ring. It is particularly advantageous, if the detector ring is displaceable in a direction that corresponds to the longitudinal main axis of the upper part of the body of a human patient who is positioned as intended, in order to be scanned in the normal use of the PET-scanning device.

In certain preferred embodiments, the PET-scanning device can comprise wheels that are attached to the main supporting structure, in order to make it easier to move the PET-scanning device. The wheels make it possible to move the PET-scanning device and to bring it to the subject to be scanned, instead of bringing the subject to the PET-scanning device. If wheels for moving the PET-scanning device are provided, the device preferably also comprises a wheel locking mechanism, in order to avoid undesired movements of the PET-scanning device particularly during the scanning of a subject.

Due to its movability, the PET-scanning device also enables in-room monitoring during a hadron therapy. For this purpose, the patient can be moved on the treatment support directly into the detector ring, which has preferably been positioned at the correct height and has been co-registered with the hadron therapy device beforehand, in order to not lose valuable time and signal from isotopic tracer decay.

In other also preferred embodiments, the PET-scanning device can comprise a scanning support in the form of for example a seating unit, i.e. a chair, or a bed, in order to accommodate the subject to be scanned. The main supporting structure can then be formed in one piece with the scanning support. The scanning support is preferably adjustable to the needs of the subject to be scanned.

For optimally position the detector ring in situations where the patient to be scanned is lying or sitting, it has turned out to be advantageous, if the two arms of the main supporting structure extend obliquely upwards in relation to the direction of gravity. Such a design of the main supporting structure is often also particularly space-saving, in particular, if the arms of the U-shaped portion form the uppermost part of the main supporting structure or, in the case that the U-shaped portion is attached to the main supporting structure, are not topped by any element of the main supporting structure.

A particularly space-saving storage of the PET-scanning device can be achieved, if the detector ring can be positioned such that the U-shaped portion, in particular the two arms of U-shaped portion, form the uppermost part of the PET-scanning device.

The main supporting structure is preferably height-adjustable, in order to position the detector ring at a desired height. For achieving this, the main supporting structure is preferably formed by an inner structure and an outer structure, which can be telescoped into each other, in order to adjust the height of the main supporting structure. Having an inner and an outer structure, which can be telescoped into each other, gives the PET-scanning device a particularly compact design.

The PET-scanning device can have an overall outer shape which narrows from the U-shaped portion downwards along the direction of gravity, in particular when viewed from a frontal direction perpendicular to the axis of rotation. With such a design, the PET-scanning device can be particularly space-saving, because the width of the device is mainly defined, at least in the upper region, by the width of the U-shaped portion needed for holding the detector ring. At the bottom, the outer shape of the PET-scanning device can broaden again along the direction of gravity, in order to improve the stability.

The PET-scanning device preferably has overall dimensions that allow the device to be moved in its normal upright position through a standard door opening having a width of not more than 98.5 cm, in particular of not more than 86.0 cm. More preferably, if the PET-scanning device has wheels, the device has an overall width that allows the PET-scanning device to be rolled forward through a door opening having a width of not more than 98.5 cm, in particular of not more than 86.0 cm.

The PET-scanning device preferably additionally comprises a computing device for carrying out an acquisition of PET-related data by means of the detector ring. The computing device usually comprises at least a processor, in particular a central processing unit, and a storage element. Pre-defined instructions are usually pre-stored in the storage element for instructing the PET-scanning device to detect emitted PET-radiation by means of the detector ring and to safe or at least cache the acquired PET-information and/or to further transmit the information to another device, e.g. by means of a wired or wireless transmission unit. The computing device is preferably integrated in the main supporting structure.

In a particularly preferred embodiment, the main supporting structure forms a through-opening together with the detector ring, if the detector ring is rotated accordingly, which through-opening extends horizontally at least through the detector ring and the main supporting structure, preferably horizontally through the entire PET-scanning device. In other words, the PET-scanning device is preferably designed such, that a subject to be scanned can be horizontally pushed through the detector ring without abutting at the main supporting structure, more preferably without abutting at any element of the PET-scanning device. This allows for example to carry out full-body scans of a lying person or to scan a plurality of rodents or plants that are moved through the device one after the other on e.g. a conveyer belt.

The axis of rotation, about which the detector ring can be rotated, preferably extends through the centre of mass of the detector ring. The detector ring can then be rotated particularly easily by the user and the load acting on the constructional components is minimized. Particularly preferred is an embodiment, in which the axis of rotation extends diametrically through the detector ring. Thus, the detector ring is preferably attached at two diametrically arranged positions of its outer surface to the two arms of the U-shaped portion.

In a particularly preferred embodiment, a guide rail is provided on each of the two arms of the U-shaped portion, and the detector ring is held in these guide rails in such a way, that it can be displaced along the guide rails. Thus, the guide rails preferably form a lateral guidance for displacing the detector ring. Guide pins or lugs can for example be attached to the outer surface of the detector ring, which guide pins or lugs engage into the guide rails, in order to enable both rotations and displacements of the detector ring with respect to the arms of the U-shaped portion. The guide rails can for example be attached to the inner surface of each arm or can be provided in the form of a slotted hole. The axis of rotation preferably extends through each of these guide rails. Lateral pulleys, helical springs, gas spring, counter weights and/or screw locks can be provided, in order to facilitate the displacement and to fix the detector ring on a certain position of the guide rails. Displacement and/or rotation of the detector ring can also be supported by a motor.

In certain embodiments, the guide rails can be rotatably attached on the two arms, such that the displacement direction, along which the detector ring can be displaced, is adjustable. Such a rotatable attachment of the guide rails on the two arms results in a particularly well adjustability of the PET-scanning device. The detector ring can in this case be optimally adjusted to the subject and to the desired imaging plane. The guide rails are advantageously rotatable about the axis of rotation of the detector ring or at least about an axis that extends in parallel to the axis of rotation of the detector ring. For this purpose, the guide rails can be rotatably attached to the inner surface of the respective arm of the U-shaped portion. Preferably, however, each arm of the U-shaped portion comprises a rotation plate, in or on which a guide rail is provided. By having a rotation plate, the loads acting on the constructional elements can be minimized and more precise adjustments become possible.

SHORT DESCRIPTION OF THE FIGURES

Figure 2A:
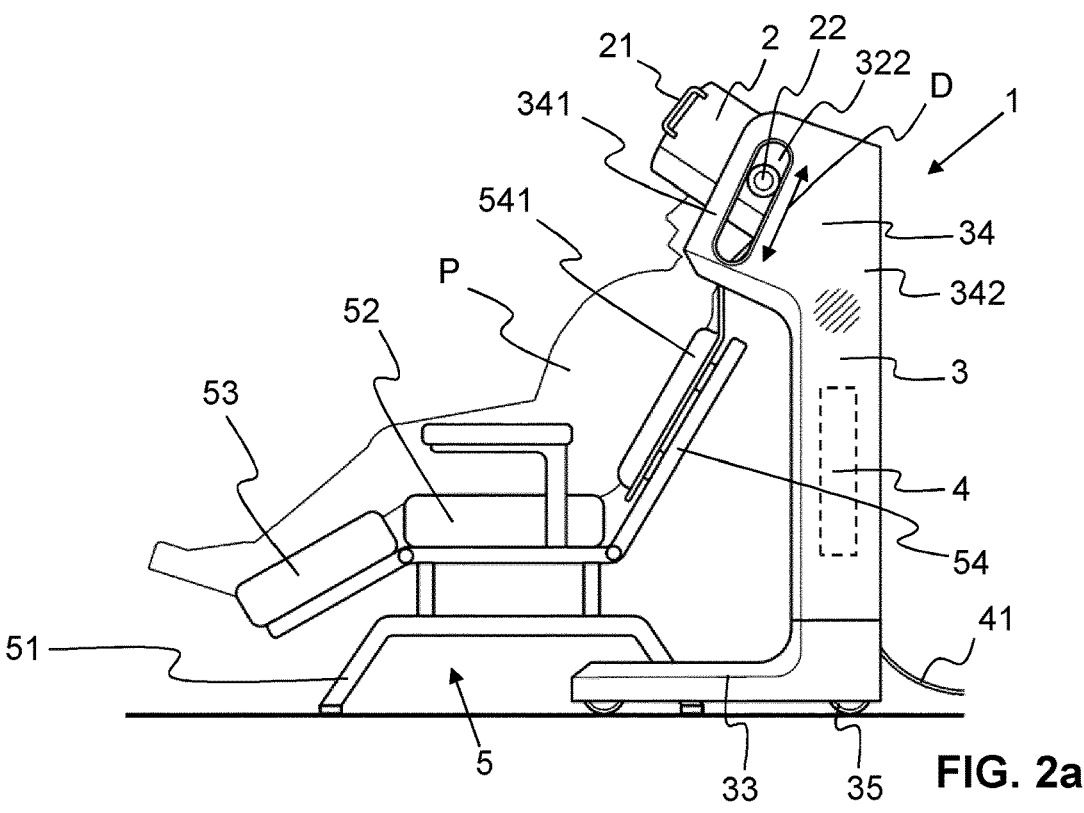
Figure 3A:
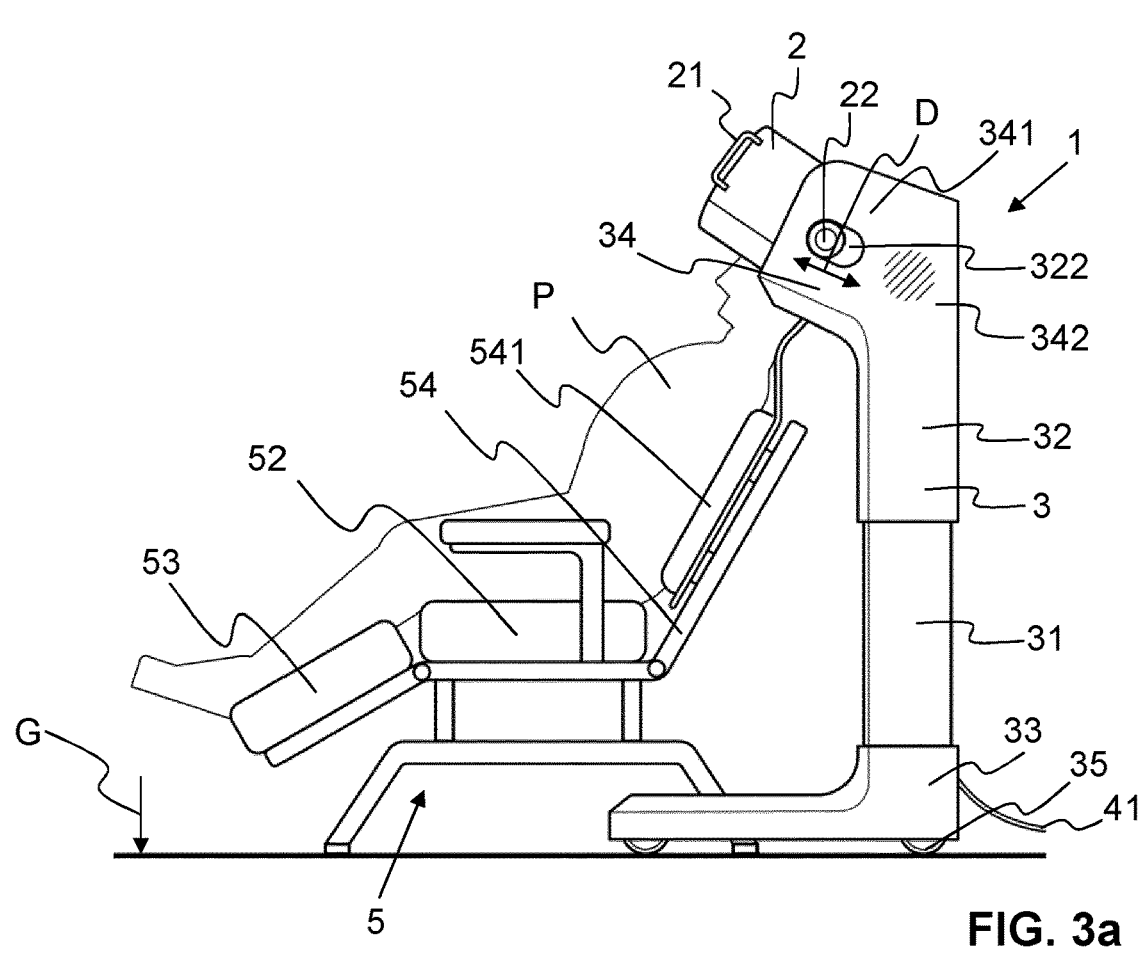
Figure 3B:
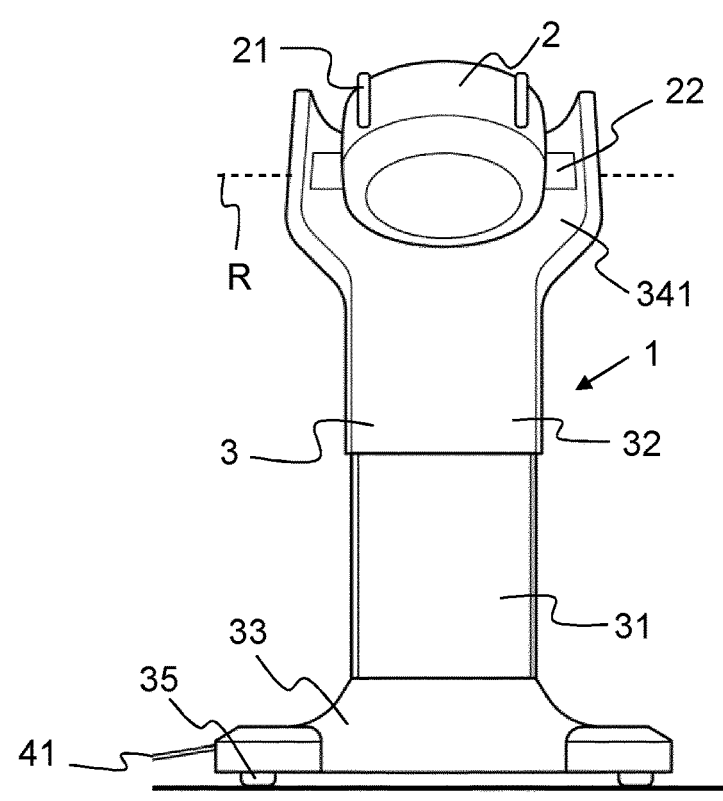
Figures 4A, 4B:
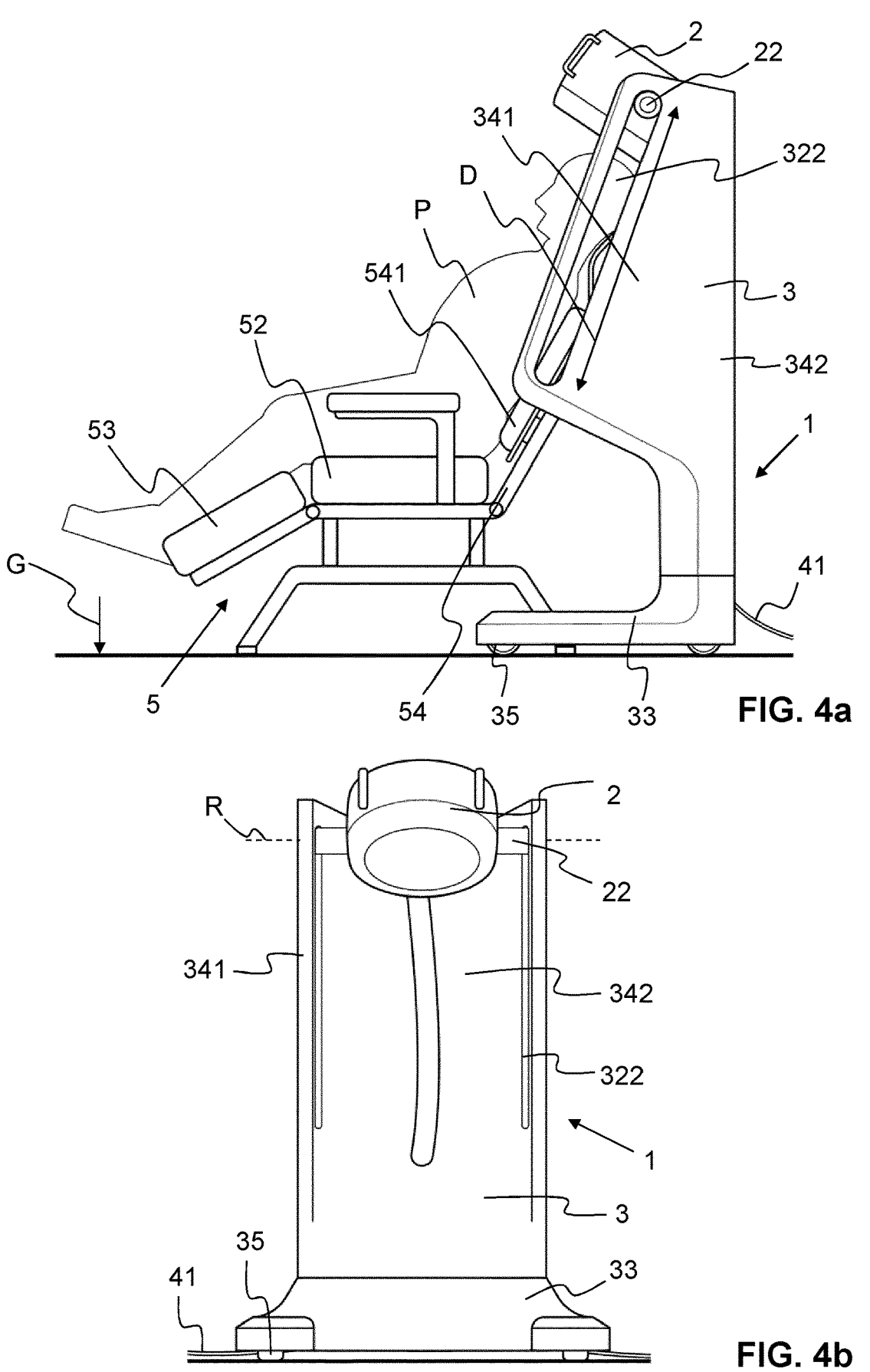
Figure 5:
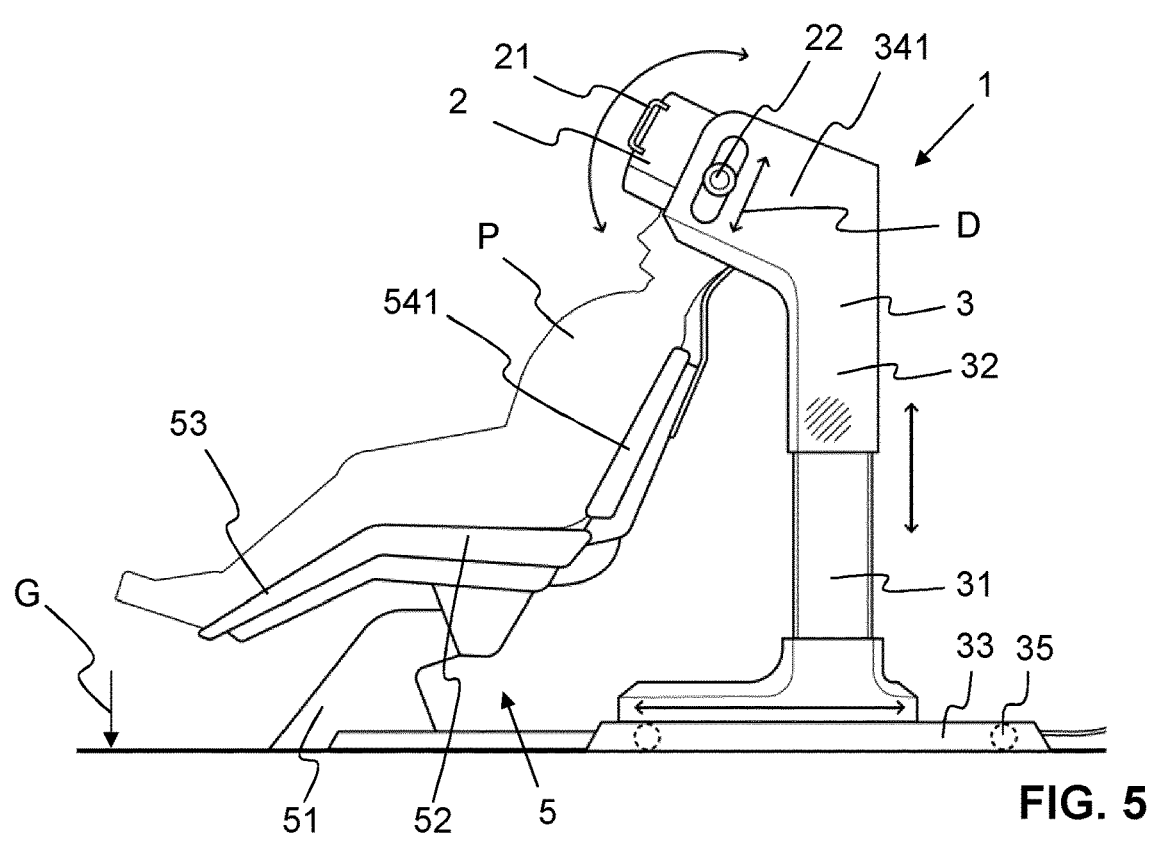
Figure 6A:
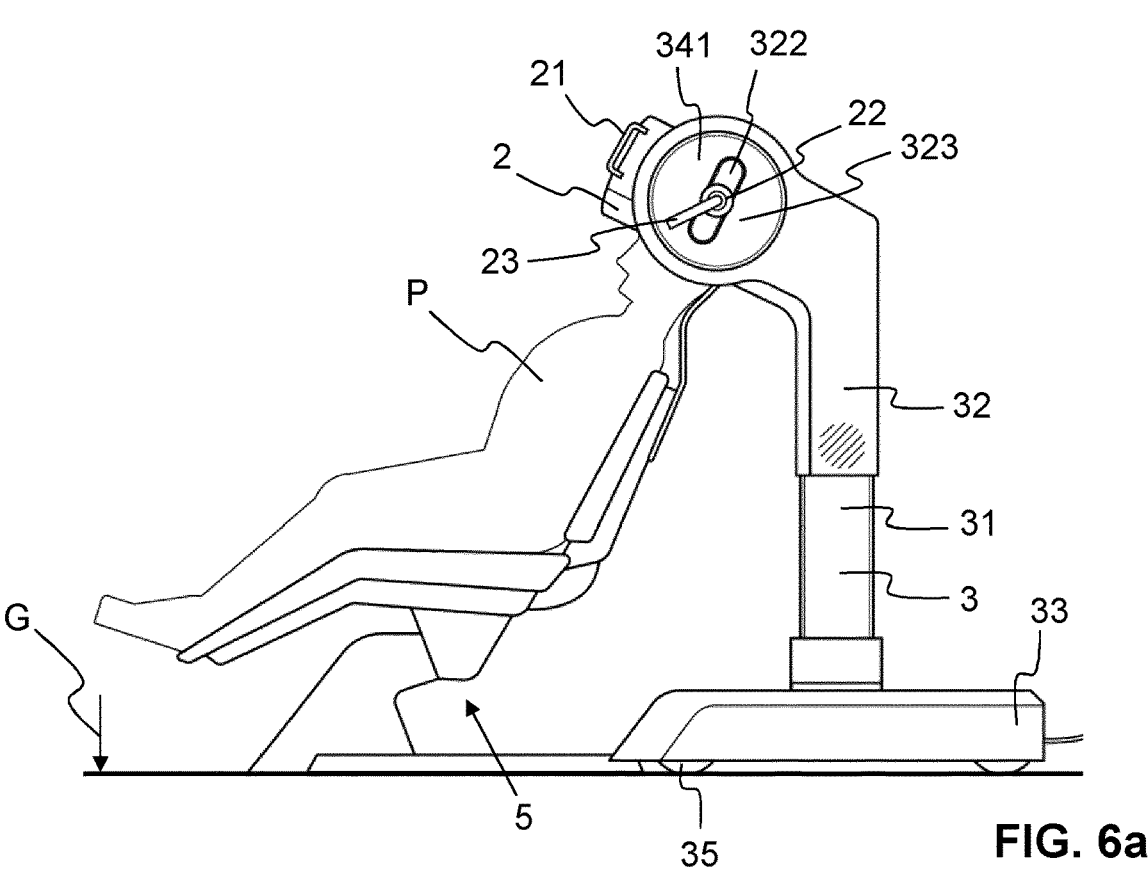
Figure 6B:
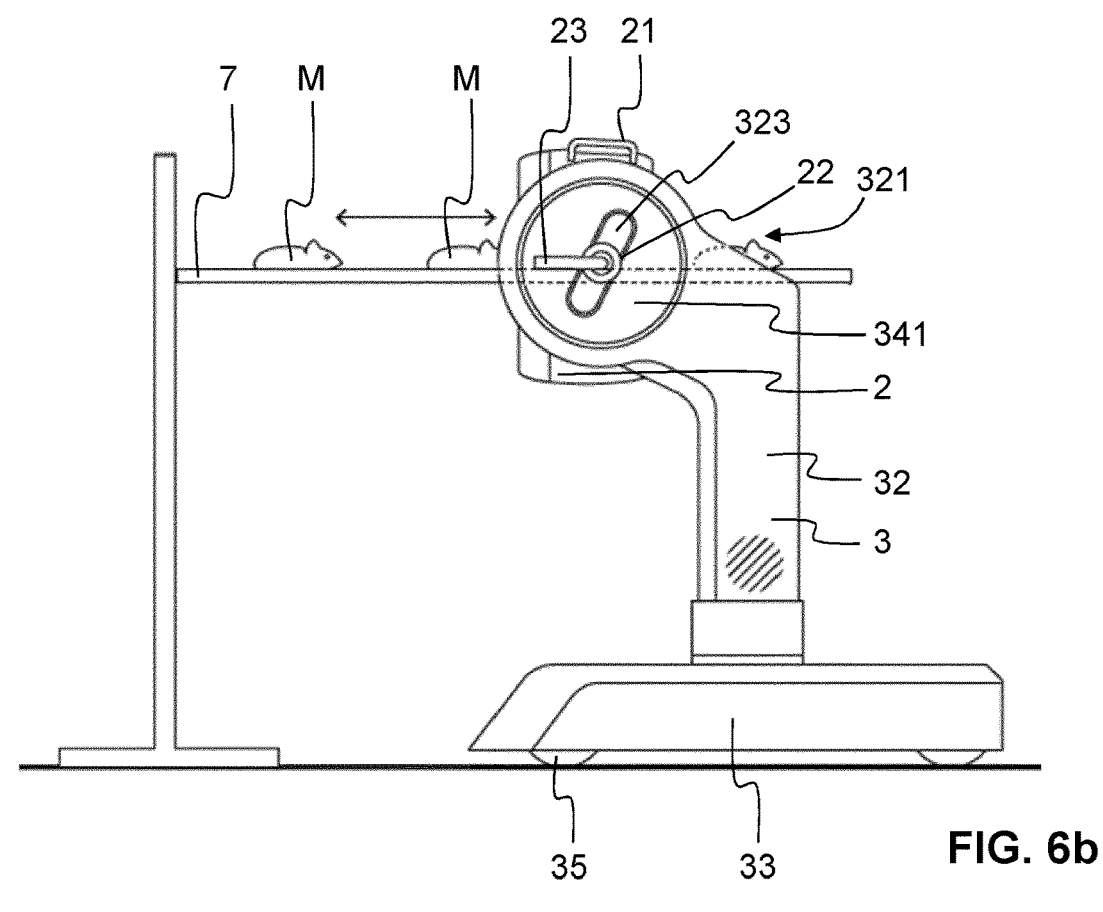
Figure 7:
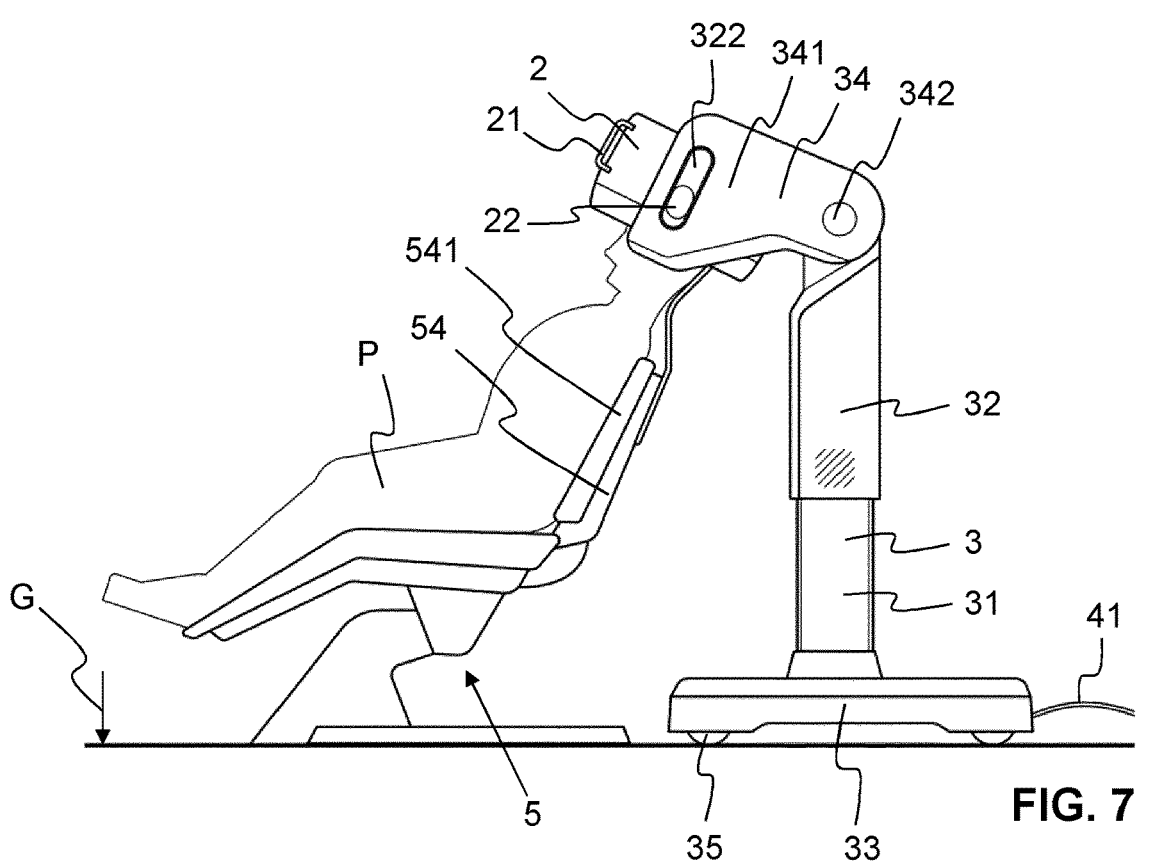

Preferred embodiments of the invention are described in the following with reference to the drawings, which only serve for illustration purposes, but have no limiting effects. In the drawings, it is shown:

FIG. 1 a side view of a first embodiment of an inventive positron emission tomography (PET)-scanning device with an integrated seating unit;

FIG. 2a a side view of a second embodiment of an inventive PET-scanning device with a separate seating unit;

FIG. 2b a front view of the PET-scanning device of FIG. 2a;

FIG. 2c a plane view on the detector ring of the PET-scanning device of FIG. 2a;

FIG. 2d a detailed side view of the bottom part of the main supporting structure of the PET-scanning device of FIG. 2a, with wheel locking mechanism;

FIG. 2e a detailed side view of the back support with adjustable backrest of the seating unit shown in FIG. 2a;

FIG. 3a a side view of a third embodiment of an inventive PET-scanning device, with height-adjustable main supporting structure, during the scanning of a patient sitting on a seating unit;

FIG. 3b a front view of the PET-scanning device of FIG. 3a;

FIG. 3c a side view of the PET-scanning device of FIG. 3a, adjusted for the scanning of a patient lying on a bed;

FIG. 3d a side view of the PET-scanning device of FIG. 3a, covered by means of a cover during storage;

FIG. 3e a side view of the PET-scanning device of FIG. 3a, adjusted for the scanning of a phantom, in order to calibrate the PET-scanning device;

FIG. 4a a side view of a fourth embodiment of an inventive PET-scanning device, with height-adjustable detector ring and with a separate seating unit;

FIG. 4b a front view of the PET-scanning device of FIG. 4a;

FIG. 4c a side view of a phantom, suited to be used for calibration of the PET-scanning device of FIG. 4a;

FIG. 4d a side view of the PET-scanning device of FIG. 4a during scanning of the phantom of FIG. 4c;

FIG. 4e a side view of the PET-scanning device of FIG. 4a, with the detector ring adjusted for scanning a patient lying on a bed;

FIG. 5 a side view of a sixth embodiment of an inventive PET-scanning device having a height-adjustable detector ring and a main supporting structure with an inner and an outer structure, the inner structure being displaceable with respect to the bottom part of the main supporting structure;

FIG. 6*a* a side view of an eighth embodiment of an inventive PET-scanning device having a height-adjustable detector ring that is mounted in guide rails provided on a rotation plate;

FIG. 6*b* a side view of the PET-scanning device of FIG. 6*a* during the scanning of a plurality of mice; and FIG. 7 a side view of a ninth embodiment of an inventive PET-scanning device having a height-adjustable detector ring that is held by a rotatable lever.

DESCRIPTION OF PREFERRED EMBODIMENTS

In FIGS. 1 to 7, several different embodiments of an inventive PET-scanning device 1 are shown. Elements that have the same or a similar function, but belong to different embodiments, are annotated with the same reference numerals in each case.

In all embodiments as shown in FIGS. 1 to 7, the PET-scanning device 1 comprises a detector ring 2, which has a plurality of sensors arranged along of its circular inner surface. The sensors, which are not visible in the Figures, serve to measure and detect the PET-radiation emitted in the region of the opening of the detector ring 2. The detector ring 2 has the basic shape of a ring in each case, with a circular inner and outer surface.

In all of the embodiments, the detector ring 2 is arranged between two holding arms 341 that hold the detector ring 2 between them. The two holding arms 341 form a part of a U-shaped portion 34, which is itself a part or is attached to a main supporting structure 3. The detector ring 2 is rotatable about an axis of rotation R that extends through the U-shaped portion 34. Furthermore, the detector ring 2 is displaceable relative to the two holding arms 341 in all embodiments. In order to facilitate rotation and displacement of the detector ring 2, one or several handles 21 are attached to the outer surface of the detector ring 2.

In the first embodiment shown in FIG. 1, the main supporting structure 3 is formed in one piece with a scanning support in the form of a seating unit 5 for accommodating a human patient P to be scanned in an inclined sitting position. The main scanning structure 3 is particularly made in one piece with a back support 54 of the seating unit 5.

The chair-like seating unit 5 comprises a base structure 51 that supports a seat base 52 to which armrests are attached. Pivotably attached to one end of the seat base 52 is an adjustable leg support 53 for supporting the legs of the patient P during the scanning procedure. On its other end, the horizontal seat base 52 merges into the inclined back support 54 via a kink. Attached to the upper side of the back support 54 are a backrest 541 and a headrest 542 for optimally accommodating the patient P during the PET-scanning procedure.

The back support 54 merges at its upper end in one piece into a U-shaped portion 34 of the main supporting structure 3. The U-shaped portion 34 has two holding arms 341. The two holding arms are connected on one end by a connection portion that is here referred to as the holding base 342. From the holding base 342, the two holding arms 341 extend in parallel in an obliquely upward direction with respect to the direction of gravity G. During the acquisition of PET-scanning images, the head of the patient P is located in the area between the two holding arms 341.

The two holding arms 341 of the U-shaped portion 34 serve to hold the detector ring 34 between them. For this purpose, two fixation lugs 22 are attached to the outer surface of the detector ring 2. The fixation lugs 22, which can also be referred to as guide lugs, are provided on diametrically opposite sides of the detector ring 2. The fixation lugs 22 engage with a guide rail 322 provided in the form of a slotted through-hole in each of the holding arms 341. The guide rails 322 extend parallel to each other and slightly inclined along the back support 54 and the backrest 541. The displacement direction D of the detector ring 2, which is defined by the longitudinal extension of the guide rails 322, approximately corresponds to the longitudinal main axis of the upper part of the body of the patient P, if the patient P sits in the seating unit 5 as intended and ready for the scanning procedure. Thus, the displacement direction D is approximately perpendicular to the longitudinal extension of the holding arms 341.

The engagement of each fixation lug 22 and the respective guide rail 322 is such, that a rotation as well as a displacement of the detector ring 2 are enabled. The axis of rotation R, about which the detector ring 2 is rotatable, is defined by the position of the fixation lugs 22. Thus, the axis of rotation R extends centrally through each of the two fixation lugs 22 and through each of the guide rails 322. With regard to the detector ring 2, the axis of rotation R extends diametrically through the ring and preferably through the centre of mass of the detector ring 2.

For carrying out the PET-image acquisition, a computing device 4 is accommodated within the main supporting structure 3. A cable 41 can be provided (see e.g. FIG. 2*a*) for data and/or energy transmission to or from the computing device 4.

For the acquisition of PET-images, the patient P is accommodated in a slightly inclined sitting position on the seating unit 5, with the detector ring 2 being in the uppermost position of the guide rails 322, as shown in FIG. 1. The detector ring 2 is then rotated and displaced by the medical personnel into an optimal position for the image acquisition using the handle 21. In order to prevent the patient P from moving his head during the image acquisition, a head strap 543 can be used as shown in FIG. 3*c*.

FIGS. 2*a* to 2*e* show a different embodiment, in which the seating unit 5 is separate from the PET-scanning device 1. The main supporting structure 3 of the PET-scanning device 1 here comprises a bottom part 33, to which wheels 35 are attached. By means of the wheels 35, the PET-scanning device 1 can be moved, in order to bring it to the patient P. From the bottom part 33, the main supporting structure 3 extends straight upwards to the U-shaped portion 34. As can be seen in the lateral view of FIG. 2*a*, the bottom part 33 extends along the holding arms 341 towards the front of the PET-scanning device 1, in order to form an overall shape of a lying U, when the PET-scanning device 1 is viewed laterally from the side. The stability of the PET-scanning device 1 is optimized by this shape.

In the frontal view of FIG. 2*b*, it can well be recognized, that the PET-scanning device 1, when viewed from the front, has an overall outer shape, which narrows from the U-shaped portion 34 downwards along the direction of gravity G and only widens at the bottom part 33. This particular outer shape of the PET-scanning device 1 is particularly space-saving and allows a stable positioning of the device at the same time. It can also been recognized that the detector ring 2 can be positioned such that it forms the uppermost part of the PET-scanning device 1.

In the plane view of FIG. 2c, it can be seen that the U-shaped portion 34 widens from the holding base 342 towards the free ends of the holding arms 341, which makes the design of the PET-scanning device 1 even more space-saving.

A detailed view of the bottom part 33 of the main supporting structure 3 is shown in FIG. 2d. As can be seen, a wheel locking mechanism 36 is provided, which allows locking the wheels 35 by means of a foot pedal 361. Upon actuation of the foot pedal 361, the wheels are retracted, in order to prevent movements of the PET-scanning device 1 especially during the imaging procedure.

FIG. 2e shows a preferred detail of the seating unit 5. In order to adapt the seating unit 5 to the patient P, the backrest 541, together with the attached headrest 542, can be moved with respect to the back support 54. In this way, the seating unit 5 can be adjusted to the size of the patient P, in order to for example not only accommodate adults, but also children.

FIGS. 3a to 3e show a further embodiment with a height-adjustable main supporting structure 3. The height-adjustment allows the PET-scanning device 1 to be optimally adjusted to the scanning situation and to store it in a particularly space-saving way. For example, a scanning of the patient P in a sitting position (FIG. 3a) or in a lying position (FIG. 3c) can be carried out with the same PET-scanning device 1. For the scanning in the lying position, the height of the main supporting structure 3 is reduced, and the patient P is accommodated on a bed 6, optionally with one or more positioning pillows 61. The possibility to adjust the height of the main supporting structure 3 also facilitates a PET-scanning in special situations, such as e.g. the scanning of animals or plants. Thus, versatility of the PET-scanning device 1 is greatly enhanced by the height-adjustability of the main supporting structure 3.

For having the possibility to adjust the height, the main supporting structure 3 comprises a lower inner structure 31 and an upper outer structure 32, that can be telescoped into each other. Due to the design with the telescopable inner and outer structures 31 and 32, the PET-scanning device 1 nevertheless has a compact and appealing design.

Different from the embodiments shown in FIGS. 1 to 2e, the embodiment of FIGS. 3a to 3e has guide rails 322 that extend approximately in a parallel direction to the holding arms 341. This allows the detector ring 2 to be displaced in such a way that it can be optimally adjusted and positioned in both situations, where the patient P is sitting (FIG. 3a) or lying (FIG. 3c).

The storage position of the PET-scanning device 1 is shown in FIG. 3d. The height of the main supporting structure 3 is minimized and the detector ring 2 is rotated in a horizontal position, such that the holding arms 341 form the uppermost part of the PET-scanning device 1. A cover 8 is used to protect the PET-scanning device from dust etc.

FIG. 3e shows a phantom positioning system 9 with a phantom 91 held by a phantom holder 92. The PET-scanning of the phantom 91 is regularly carried out, in order to adjust and calibrate the scanning parameters of the PET-scanning device 1. As can be seen, the phantom 91 extends horizontally from the phantom holder 92, in order to be moved into the detector ring 2 along a horizontal direction. The height of the PET-scanning device 1 is minimized and the detector ring 2 is rotated in a vertical position for this purpose.

FIGS. 4a to 4e show an embodiment, in which the main supporting structure 3 is fixed as concerns its height. In order to nevertheless enable PET-scans in the sitting position (FIG. 4a) and in the lying position (FIG. 4e) of the patient P by means of the PET-scanning device 1, the guide rails 322 with the holding arms 341 of the U-shaped portion 34 extend over approximately half or even more of the height of the main supporting structure 3. This allows positioning the detector ring 2 on a large variety of heights. For the scanning of the patient P in a lying position (FIG. 4e) and for scanning the phantom 91 (FIG. 4d), the detector ring 2 can be displaced to its lowermost position, and for scanning the patient P in an inclined sitting position (FIG. 4a), the detector ring 2 can be displaced to its uppermost position.

FIG. 5 shows an embodiment in which the main supporting structure 3 is height-adjustable similar as in the embodiment of FIGS. 3a to 3e. Here, however, not only the main supporting structure 3 is height adjustable, but also the detector ring 2 is height-adjustable over a considerable range with respect to the U-shaped portion 34. The displacement of the detector ring 2 can be used for fine-adjusting the detector ring 2 to the desired imaging plane, which facilitates the handling of the PET-scanning device 1 in preparation of the actual imaging. Additionally, the inner structure 31 is here displaceable relative to the bottom part 33 of the main supporting structure, which can also be used to fine adjust the PET-scanning device 1 to the patient P and to the desired imaging plane.

In the embodiment of FIGS. 6a and 6b, the guide rails 322 are in each case provided within a rotation plate 323 that forms a part of the respective holding arm 341. The rotation plates 323, which are rotatable, bring about the advantage, that the guide rails 322 can be rotated about the axis of rotation R, in order to adjust the displacement direction D. The additional adjustability of the displacement direction D greatly improves the adjustability of the PET-scanning device 1 to different patients P and to different scanning situations in general. Thus, the versatility of the PET-scanning device 1 can be further improved owing to the rotation plates 323. An adjustment handle 23 is provided for rotating the rotation plates 323.

In all embodiments, it is preferred that the main supporting structure 3 comprises a through-opening 321, in the form of e.g. a recess, which extends horizontally through the main supporting structure 3 in such a way, that the detector ring 2 with its inner opening can be positioned flush with regard to this through-opening 321, as shown in FIG. 6b. For this purpose, the detector ring 2 is rotation in a vertical position. The through-opening 321 then allows pushing a scanning support 7 completely through the detector ring 2 along the horizontal direction without abutting at the main supporting structure 3 or at any other part of the PET-scanning device 1. With such a design of the PET-scanning device 1, whole body scans become for example possible by pushing a lying person through a correspondingly dimensioned detector ring 2. Also, as shown in FIG. 6b, a plurality of animals, such as e.g. mice M, can be scanned one after the other, if they are arranged on a scanning support 7 which is horizontally pushed through the detector ring 2 or which even has a conveyer belt for moving the mice M one after the other through the detector ring 2.

A further inventive embodiment of a PET-scanning device 1 is shown in FIG. 7. The device here also has a height-adjustable main supporting structure 3 with an inner structure 31 and an outer structure 32, that are telescopable into each other. The U-shaped portion 34 of this embodiment does not form a part of the main supporting structure 3 but is attached to the top of the outer structure 32 of the main supporting structure 3. The U-shaped portion 34 is such attached to the main supporting structure 3, that it can be rotated about a horizontally extending axis that extends through the holding base 342 of the U-shaped portion 34. The axis, about which the U-shaped portion 34 can be rotated, particularly extends in parallel to the longitudinal main direction of the holding base 342. Since the detector ring 2 is held between the two holding arms 341 of the U-shaped portion 34, the detector ring 2 can be rotated, together with the U-shaped portion 34, about the axis of rotation which horizontally extends through the holding base 342 of the U-shaped portion 34. This allows the detector ring 2 not only to be rotated, but at the same time to be lowered with respect to the direction of gravity G. Additionally, the detector ring 2 can be displaced within the guide rails 322 relative to the holding arms 341, in order to optimally adjust the detector ring 2 to the desired imaging plane. Rotation of the detector ring 2 with respect to the holding arms 341 is not possible in the current embodiment but could of course be enabled in other embodiments.

The invention is of course not limited to the preceding presented embodiments and a plurality of modifications is possible. For example, the displaceability of the detector ring 2 with respect to the holding arms 341 does not necessarily be provided by means of guide rails arranged on the holding arms. The guide rails could e.g. also be arranged on the detector ring and fixation lugs that engage in the guide rails could be attached to the holding arms. Wheels for making it easier to move of the PET-scanning device are preferred to be provided in all embodiments, but they could also be omitted. Features that have been indicated with respect to certain embodiments only can well be provided on other embodiments, too. A plurality of further modifications is possible.

| REFERENCE NUMERALS | | | |
|---|---|---|---|
| 1 | PET-scanning device | 51 | Base structure |
| 2 | Detector ring | 52 | Seat base |
| 21 | Handle | 53 | Leg support |
| 22 | Fixation lug | 54 | Back support |
| 23 | Adjustment handle | 541 | Backrest |
| 3 | Main supporting structure | 542 | Headrest |
| 31 | Inner structure | 543 | Head strap |
| 32 | Outer structure | 6 | Bed |
| 321 | Through-opening | 61 | Positioning pillow |
| 322 | Guide rail | 7 | Scanning support |
| 323 | Rotation plate | 8 | Cover |
| 33 | Bottom part | 9 | Phantom positioning system |
| 34 | U-shaped portion | 91 | Phantom |
| 341 | Holding arm | 92 | Phantom holder |
| 342 | Holding base | P | Patient |
| 35 | Wheel | M | Mouse |
| 36 | Wheel locking mechanism | R | Axis of rotation |
| 361 | Foot pedal | D | Displacement direction |
| 4 | Computing device | G | Direction of gravity |
| 41 | Cable | | |
| 5 | Seating unit | | |

The invention claimed is:

1. A positron emission tomography (PET)-scanning device comprising:

a detector ring for detecting emitted PET-radiation; and a main supporting structure which has or to which is attached a U-shaped portion with two arms configured to hold the detector ring between the two arms, wherein the detector ring is held by the two arms in such a way that the detector ring can be rotated about an axis of rotation that extends through the U-shaped portion and the detector ring can be displaced relative to the two arms, wherein guide rails are on the two arms, respectively, or on the detector ring, and the guide rails are configured to hold the detector ring such that the detector ring is configured to be displaced along the two arms, and wherein the PET-scanning device further comprises lugs that are engaged into the guide rails, and are attached to an outer surface of the detector ring or to the two arms.

2. The PET-scanning device of claim 1, further comprising wheels, that are attached to the main supporting structure, in order to make it easier to move the PET-scanning device.

3. The PET-scanning device of claim 2, further comprising a wheel locking mechanism for locking the wheels.

4. The PET-scanning device according to claim 1, wherein the two arms of the U-shaped portion extend obliquely upwards in relation to the direction of gravity.

5. The PET-scanning device according to claim 1, wherein the detector ring is configured to be positioned such that the two arms of the U-shaped portion form an uppermost part of the PET-scanning device.

6. The PET-scanning device according to claim 1, wherein the main supporting structure is height-adjustable, in order to position the detector ring at a desired height.

7. The PET-scanning device according to claim 6, wherein the main supporting structure comprises an inner structure and an outer structure, wherein the inner structure and the outer structure are configured to be telescoped into each other such as to adjust a height of the main supporting structure.

8. The PET-scanning device according to claim 1, wherein the PET-scanning device has an overall outer shape which narrows from the U-shaped portion downwards along the direction of gravity.

9. The PET-scanning device according to claim 1, wherein the PET-scanning device has overall dimensions that allow the PET-scanning device to be moved in its normal upright position through a door opening having a width of not more than 98.5 cm.

10. The PET-scanning device according to claim 1, further comprising a computing device configured to carry out an acquisition of PET-related data by the detector ring, the computing device being integrated in the main supporting structure.

11. The PET-scanning device according to claim 1, wherein the main supporting structure together with the detector ring forms a through-opening, if the detector ring is rotated accordingly, which through-opening extends horizontally at least through the detector ring and the main supporting structure.

12. The PET-scanning device according to claim 1, wherein the axis of rotation, about which the detector ring can be rotated, extends through a center of mass of the detector ring.

13. The PET-scanning device according to claim 1, wherein the axis of rotation extends through each of the guide rails.

14. The PET-scanning device according to claim 1, wherein the guide rails are rotatably attached on the two arms, such that a displacement direction, along which the detector ring can be displaced, is adjustable.

15. The PET-scanning device according to claim 1, additionally comprising an adjustable seating unit, which allows a human patient to sit during a PET-scanning procedure.

16. The PET-scanning device according to claim 1, wherein the axis of rotation extends through the two arms of the U-shaped portion.

17. The PET-scanning device according to claim 1, wherein the axis of rotation extends through the lugs, and the lugs are configured to change a position of the axis of rotation by relative movement of the lugs with respect to the guide rails in an extending direction of the guide rails.

18. The PET-scanning device according to claim 17, wherein the two arms comprise rotation plates that are configured to change the extending direction of the guide rails by rotating the guide rails; or the U-shaped portion is connected to the main supporting structure by a holding base, and the U-shaped portion is configured to change the extending direction of the guide rails by the U-shaped portion rotating, via the holding base, with respect to the main supporting structure.

* * * * *